United States Patent
Scheckel

(10) Patent No.: US 9,404,505 B2
(45) Date of Patent: *Aug. 2, 2016

(54) FLUID PUMP WITH A ROTOR

(71) Applicant: ECP ENTWICKLUNGSGESELLSCHAFT MBH, Berlin (DE)

(72) Inventor: Mario Scheckel, Berlin (DE)

(73) Assignee: ECP ENTWICKLUNGSGESELLSCHAFT MBH, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/638,587

(22) Filed: Mar. 4, 2015

(65) Prior Publication Data

US 2015/0211542 A1 Jul. 30, 2015

Related U.S. Application Data

(63) Continuation of application No. 14/275,182, filed on May 12, 2014, now Pat. No. 8,998,792, which is a continuation of application No. 13/132,385, filed as application No. PCT/EP2009/008858 on Dec. 4, 2009, now Pat. No. 8,721,516.

(60) Provisional application No. 61/120,095, filed on Dec. 5, 2008.

(30) Foreign Application Priority Data

Dec. 5, 2008 (EP) .................................. 08075923

(51) Int. Cl.
*A61M 1/10* (2006.01)
*F04D 29/18* (2006.01)
(Continued)

(52) U.S. Cl.
CPC ............... *F04D 29/18* (2013.01); *A61M 1/101* (2013.01); *A61M 1/1024* (2014.02); *A61M 1/125* (2014.02);
(Continued)

(58) Field of Classification Search
None
See application file for complete search history.

(56) References Cited

U.S. PATENT DOCUMENTS 2,350,534 A 6/1944 Rosinger
2,533,716 A 12/1950 Coursey
(Continued)

FOREIGN PATENT DOCUMENTS

CA 1008330 A 4/1977
CA 2311977 A1 12/2000
(Continued)

OTHER PUBLICATIONS

Brochure Impella Pumpsystem of Impella CardioSystems AG, "Turning Lives Around," Aug. 2003 (4 pages).
Buecker A et al., "Use of a Nonmetallic Guide Wire for Magnetic Resonance—Guided Coronary Artery Catheterization," Investigative Radiology, 39:11, pp. 656-660 (2004).
(Continued)

*Primary Examiner* — Brian T Gedeon
*Assistant Examiner* — Ankit D Tejani
(74) *Attorney, Agent, or Firm* — Ropes & Gray LLP

(57) ABSTRACT

The invention relates to a fluid pump, in particular to a liquid pump having a rotor with at last one rotor blade for conveying the fluid, the rotor being variable with respect to its diameter between a first, compressed state and a second expanded state. In order to produce a simple compressibility and expandability of the rotor of the pump, it is provided according to the invention that at least one rotor blade is deformable between a first state which it assumes in the compressed state of the rotor and a second state which it assumes in the expanded state of the rotor by means of a fluid counterpressure during a rotation of the rotor during pump operation.

28 Claims, 7 Drawing Sheets

(51) Int. Cl.
  *F04D 29/02* (2006.01)
  *F04D 29/24* (2006.01)
  *A61M 1/12* (2006.01)
  *F04D 29/60* (2006.01)

(52) U.S. Cl.
  CPC ............ *F04D 29/026* (2013.01); *F04D 29/247* (2013.01); *F04D 29/605* (2013.01); *Y10T 29/49229* (2015.01); *Y10T 29/49245* (2015.01)

(56) References Cited

U.S. PATENT DOCUMENTS

| | | |
|---|---|---|
| 3,333,127 A | 7/1967 | Congdon et al. |
| 3,354,833 A | 11/1967 | Laing |
| 3,489,145 A | 1/1970 | Judson et al. |
| 3,510,229 A | 5/1970 | Smith et al. |
| 3,568,659 A | 3/1971 | Karnegis |
| 3,802,551 A | 4/1974 | Somers |
| 3,812,812 A | 5/1974 | Hurwitz |
| 3,846,045 A | 11/1974 | Mincuzzi |
| 3,936,683 A | 2/1976 | Walker |
| 4,014,317 A | 3/1977 | Bruno |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,207,028 A | 6/1980 | Ridder |
| 4,420,851 A | 12/1983 | Wiener |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier et al. |
| 4,801,243 A | 1/1989 | Norton |
| 4,817,613 A | 4/1989 | Jaraczewski et al. |
| 4,846,152 A | 7/1989 | Wampler et al. |
| 4,895,557 A | 1/1990 | Moise et al. |
| 4,919,647 A | 4/1990 | Nash |
| 4,957,504 A | 9/1990 | Chardack |
| 4,969,865 A | 11/1990 | Hwang et al. |
| 4,984,972 A | 1/1991 | Clausen et al. |
| 4,995,857 A | 2/1991 | Arnold |
| 5,011,469 A | 4/1991 | Buckberg et al. |
| 5,017,103 A | 5/1991 | Dahl |
| 5,037,403 A | 8/1991 | Garcia |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,147,186 A | 9/1992 | Buckholtz |
| 5,158,279 A | 10/1992 | Laffey et al. |
| 5,163,431 A | 11/1992 | Griep |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,250,059 A | 10/1993 | Andreas et al. |
| 5,275,580 A | 1/1994 | Yamazaki |
| 5,357,963 A | 10/1994 | Mayol et al. |
| 5,373,619 A | 12/1994 | Fleischhacker et al. |
| 5,376,114 A | 12/1994 | Jarvik |
| 5,405,383 A | 4/1995 | Barr |
| 5,421,338 A | 6/1995 | Crowley et al. |
| 5,480,392 A | 1/1996 | Mous |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,827,171 A | 10/1998 | Dobak, III et al. |
| 5,851,174 A | 12/1998 | Jarvik et al. |
| 5,863,179 A | 1/1999 | Westphal et al. |
| 5,882,329 A | 3/1999 | Patterson et al. |
| 5,888,241 A | 3/1999 | Jarvik |
| 5,897,299 A | 4/1999 | Fukunaga |
| 5,938,672 A | 8/1999 | Nash |
| 5,954,745 A | 9/1999 | Gertler et al. |
| 6,001,078 A | 12/1999 | Reekers |
| 6,030,397 A | 2/2000 | Monetti et al. |
| 6,054,788 A | 4/2000 | Dombrovski et al. |
| 6,083,260 A | 7/2000 | Aboul-Hosn |
| 6,123,725 A | 9/2000 | Aboul-Hosn |
| 6,129,704 A | 10/2000 | Forman et al. |
| 6,152,693 A | 11/2000 | Olsen et al. |
| 6,168,624 B1 | 1/2001 | Sudai |
| 6,183,220 B1 | 2/2001 | Ohara et al. |
| 6,245,007 B1 | 6/2001 | Bedingham et al. |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,413,222 B1 | 7/2002 | Pantages et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,517,528 B1 | 2/2003 | Pantages et al. |
| 6,533,716 B1 | 3/2003 | Schmitz-Rode et al. |
| 6,537,030 B1 | 3/2003 | Garrison |
| 6,537,247 B2 | 3/2003 | Shannon |
| 6,537,315 B2 | 3/2003 | Yamazaki et al. |
| 6,544,216 B1 | 4/2003 | Sammler et al. |
| 6,592,612 B1 | 7/2003 | Samson et al. |
| 6,652,548 B2 | 11/2003 | Evans et al. |
| 6,719,791 B1 | 4/2004 | Nusser et al. |
| 6,841,910 B2 | 1/2005 | Gery |
| 6,858,001 B1 | 2/2005 | Aboul-Hosn |
| 6,860,713 B2 | 3/2005 | Hoover |
| 6,945,977 B2 | 9/2005 | Demarais et al. |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,467,929 B2 | 12/2008 | Nusser et al. |
| 7,646,376 B2 | 1/2010 | Blersch |
| 7,731,675 B2 | 6/2010 | Aboul-Hosn et al. |
| 7,841,976 B2 | 11/2010 | McBride |
| 7,927,068 B2 | 4/2011 | McBride et al. |
| 7,934,909 B2 | 5/2011 | Nuesser et al. |
| 8,079,948 B2 | 12/2011 | Shifflette |
| 8,439,859 B2 | 5/2013 | Pfeffer et al. |
| 8,888,728 B2 | 11/2014 | Aboul-Hosn et al. |
| 8,998,792 B2 | 4/2015 | Scheckel |
| 2001/0000528 A1 | 4/2001 | Cho |
| 2002/0123661 A1 | 9/2002 | Verkerke et al. |
| 2002/0151799 A1 | 10/2002 | Pantages et al. |
| 2002/0183840 A1 | 12/2002 | Lapeyre et al. |
| 2003/0135940 A1 | 7/2003 | Lev et al. |
| 2003/0208097 A1 | 11/2003 | Aboul-Hosn et al. |
| 2003/0231959 A1 | 12/2003 | Snider |
| 2004/0022640 A1 | 2/2004 | Siess et al. |
| 2004/0044266 A1 | 3/2004 | Siess et al. |

(56) References Cited

U.S. PATENT DOCUMENTS

| | | |
|---|---|---|
| 2004/0046466 A1 | 3/2004 | Siess et al. |
| 2004/0093074 A1 | 5/2004 | Hildebrand et al. |
| 2004/0113502 A1 | 6/2004 | Li et al. |
| 2004/0193046 A1 | 9/2004 | Nash et al. |
| 2004/0215222 A1 | 10/2004 | Krivoruchko |
| 2004/0215228 A1 | 10/2004 | Simpson et al. |
| 2004/0260237 A1 | 12/2004 | Squadrito |
| 2005/0135942 A1 | 6/2005 | Wood et al. |
| 2005/0180854 A1* | 8/2005 | Grabau et al. ............ 416/241 R |
| 2006/0008349 A1 | 1/2006 | Khaw |
| 2006/0062672 A1* | 3/2006 | McBride et al. ............. 416/142 |
| 2006/0195004 A1 | 8/2006 | Jarvik |
| 2006/0198736 A1 | 9/2006 | Rousseau |
| 2007/0093887 A1* | 4/2007 | Case et al. ................... 623/1.24 |
| 2007/0118072 A1 | 5/2007 | Nash |
| 2007/0213761 A1 | 9/2007 | Murphy et al. |
| 2008/0004571 A1 | 1/2008 | Voss |
| 2008/0103591 A1 | 5/2008 | Siess |
| 2008/0132747 A1 | 6/2008 | Shifflette |
| 2008/0132748 A1 | 6/2008 | Shifflette |
| 2008/0183136 A1 | 7/2008 | Lenker et al. |
| 2008/0262584 A1 | 10/2008 | Bottomley et al. |
| 2008/0306327 A1 | 12/2008 | Shifflette |
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0171137 A1 | 7/2009 | Farnan |
| 2009/0218728 A1 | 9/2009 | Moyer |
| 2009/0227892 A1 | 9/2009 | Krombach et al. |
| 2010/0041939 A1 | 2/2010 | Siess |
| 2010/0210895 A1 | 8/2010 | Aboul-Hosn et al. |
| 2010/0268017 A1 | 10/2010 | Siess |
| 2011/0004046 A1 | 1/2011 | Campbell et al. |
| 2011/0071338 A1 | 3/2011 | McBride et al. |
| 2011/0236210 A1 | 9/2011 | McBride |
| 2011/0238172 A1 | 9/2011 | Akdis |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0066140 A1 | 3/2013 | McBride et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |
| 2015/0073202 A1 | 3/2015 | Aboul-Hosn et al. |

FOREIGN PATENT DOCUMENTS

| | | |
|---|---|---|
| CA | 2613175 A1 | 1/2007 |
| CA | 2632420 A1 | 6/2007 |
| CA | 2701809 A1 | 4/2009 |
| CA | 2701810 A1 | 4/2009 |
| CN | 101278127 | 10/2008 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 4414903 A1 | 11/1995 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 100 59 714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102005039950 A1 | 3/2007 |
| DE | 102010011998 A1 | 9/2010 |
| EP | 0166104 | 1/1986 |
| EP | 0364293 A2 | 4/1990 |
| EP | 0445782 A1 | 9/1991 |
| EP | 0480102 A1 | 4/1992 |
| EP | 0560000 A2 | 9/1993 |
| EP | 0629412 A2 | 12/1994 |
| EP | 0768091 A1 | 4/1997 |
| EP | 0768900 A1 | 4/1997 |
| EP | 0884064 A2 | 12/1998 |
| EP | 0914171 A2 | 5/1999 |
| EP | 0916359 A1 | 5/1999 |
| EP | 951302 A2 | 10/1999 |
| EP | 1019117 A1 | 7/2000 |
| EP | 1034808 A1 | 9/2000 |
| EP | 1066851 A1 | 1/2001 |
| EP | 1114648 A2 | 7/2001 |
| EP | 1207934 A2 | 5/2002 |
| EP | 1337288 A1 | 8/2003 |
| EP | 1651290 A1 | 5/2006 |
| EP | 2047872 A1 | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| FR | 2788223 A1 | 7/2000 |
| GB | 2239675 A | 7/1991 |
| JP | H04126158 A | 4/1992 |
| RU | 2229899 C2 | 6/2004 |
| WO | WO-9202263 A1 | 2/1992 |
| WO | WO-9302732 A1 | 2/1993 |
| WO | WO-9303786 A1 | 3/1993 |
| WO | WO-9314805 A1 | 8/1993 |
| WO | WO-9401148 A1 | 1/1994 |
| WO | WO-9405347 A1 | 3/1994 |
| WO | WO-9409835 A1 | 5/1994 |
| WO | WO-9420165 A2 | 9/1994 |
| WO | WO-9523000 A2 | 8/1995 |
| WO | WO-9618358 A1 | 6/1996 |
| WO | WO-9625969 A2 | 8/1996 |
| WO | WO-9744071 A1 | 11/1997 |
| WO | WO-9853864 A1 | 12/1998 |
| WO | WO-9919017 A1 | 4/1999 |
| WO | WO-9944651 A1 | 9/1999 |
| WO | WO-99/58170 A1 | 11/1999 |
| WO | WO-0019097 | 4/2000 |
| WO | WO-0027446 A1 | 5/2000 |
| WO | WO-0043053 | 7/2000 |

(56) References Cited

FOREIGN PATENT DOCUMENTS

| | | |
|---|---|---|
| WO | WO-0043054 A2 | 7/2000 |
| WO | WO-0062842 A1 | 10/2000 |
| WO | WO-0107760 | 2/2001 |
| WO | WO-0107787 | 2/2001 |
| WO | WO-0183016 | 11/2001 |
| WO | WO-0222200 | 3/2002 |
| WO | WO-02/43791 A1 | 6/2002 |
| WO | WO-0243791 | 6/2002 |
| WO | WO-03057013 | 7/2003 |
| WO | WO-03103745 | 12/2003 |
| WO | WO-2005002646 A1 | 1/2005 |
| WO | WO-2005016416 A1 | 2/2005 |
| WO | WO-2005021078 A1 | 3/2005 |
| WO | WO-2005030316 A1 | 4/2005 |
| WO | WO-2005032620 A1 | 4/2005 |
| WO | WO-2005081681 A2 | 9/2005 |
| WO | WO-2006020942 A1 | 2/2006 |
| WO | WO-2006034158 A2 | 3/2006 |
| WO | WO-2006133209 A1 | 12/2006 |
| WO | WO-2007003351 A1 | 1/2007 |
| WO | WO-2007103390 A2 | 9/2007 |
| WO | WO-2007103464 A2 | 9/2007 |
| WO | WO-2007112033 A2 | 10/2007 |
| WO | WO-2008017289 A2 | 2/2008 |
| WO | WO-2008034068 A2 | 3/2008 |
| WO | WO-2008054699 A2 | 5/2008 |
| WO | WO-2008106103 A2 | 9/2008 |
| WO | WO-2008116765 A2 | 10/2008 |
| WO | WO-2008124696 A1 | 10/2008 |
| WO | WO-2008137352 A1 | 11/2008 |
| WO | WO-2008137353 A1 | 11/2008 |
| WO | WO-2009015784 A1 | 2/2009 |
| WO | WO-2010063494 A1 | 6/2010 |
| WO | WO-2010133567 A1 | 11/2010 |
| WO | WO-2013034547 A1 | 3/2013 |
| WO | WO-2013092971 A1 | 6/2013 |
| WO | WO-2013093001 A2 | 6/2013 |
| WO | WO-2013093058 A1 | 6/2013 |

OTHER PUBLICATIONS

Compendium of Technical and Scientific Information for the Hemopump Temporary Cardiac Assist System, 1988 (15 pages).

Dekker, Andre, et al, "Efficacy of a New Intraaortic Propeller Pump vs the Intraaortic Balloon Pump," Chest Journal; Jun. 2003 (7 pages).

Frazier, O.H., et al, "First Human Use of the Hemopump, A Cather-Mounted Ventricular Assist Device," Ann Thorac Surg., Feb; 49(2): pp. 299-304 (1990).

International Preliminary Report on Patentability, from PCT/EP09/008858, issued Jun. 7, 2011. (5 pages).

Jomed Reitan Catheter Pump Brochure, www.jomed.com/rcp (undated) (6 pages).

Lueger, Lexikon der Technik, "Lexikon der Feinwerktechnik", vol. 13, Deutsche Verlags-Anstalt GmbH, Stuttgart, seite 551 (4 pages) (1968).

Reitan, Oyvind et al, "Hydrodynamic Properties of a New Percutaneous Intra-aortic Axial Flow Pump," ASAIO Journal; May-June; vol. 16; 6 pages (2000).

Rothman, Martin T, "Tthe Reitan Catheter Pump: A New Versatile Approach for Hemodynamic Support," London Chest Hospital Barts & The Long NHS Trust, presented at TCT Conference, Oct. 24-26, 2006, (40 pages).

Schmitz-Rode, T et al., "An Expandable Percutaneous Catheter Pump for Left Ventricular Support," Journal of the American College of Cardiology, 45:11, pp. 1856-1861 (2005).

Schmitz-Rode, T et al, "Temporary Pulmonary Stent Placement as Emergency Treatment of Pulmonary Embolism," Journal of the American College of Cardiology, 48:4, pp. 812-816 (2006).

Siess, Thorsten, "Systemanalyse und Entwicklung intravasaler Rotationspumpen zur Herzunterstutzung," Helmholtz-Institut, Jun. 24, 1998 (105 pages) and partial English translation (39 pages).

Verma, R et al., "Evaluation of a Newly Developed Percutaneous Thrombectomy Basket Device in Sheep with Central Pulmonary Embolisms," Investigative Radiology, 41:10, pp. 729-734 (2006).

Wampler, Richard, K., "In Vivo Evaluation of a Peripheral Vascular Access Axial Flow Blood Pump," ASAIO Trans., July-September;34(3): pp. 450-454 (1988).

\* cited by examiner

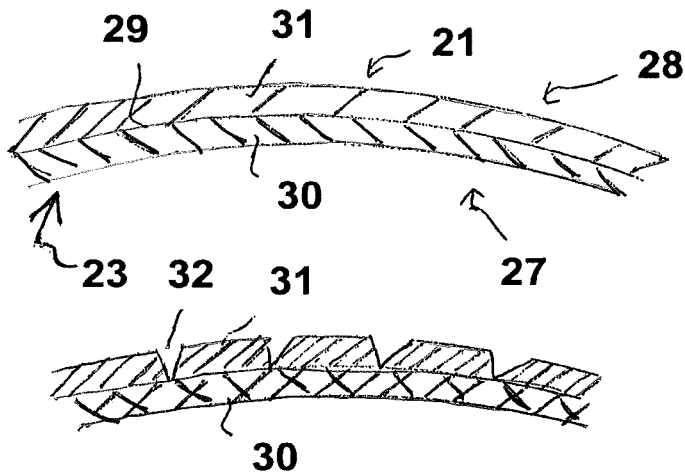
Fig. 5
Fig. 6
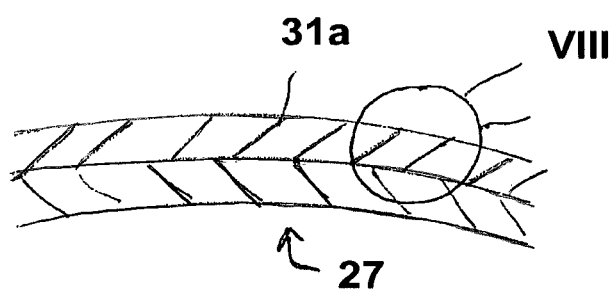
Fig. 7
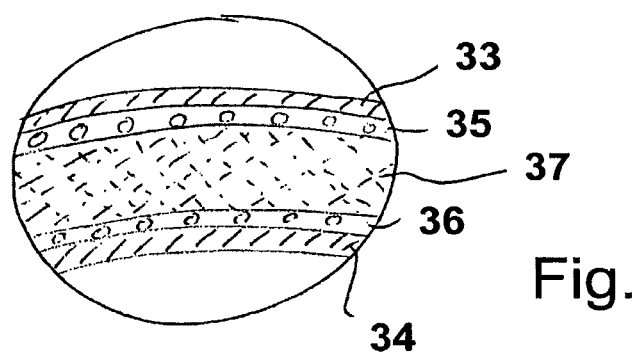
Fig. 8
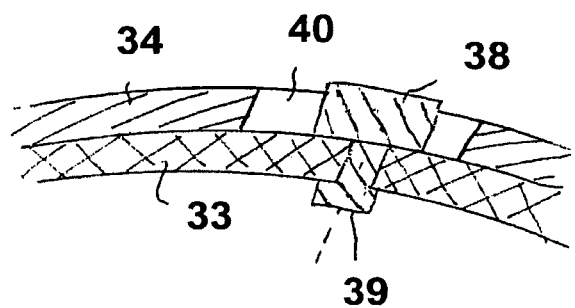
Fig. 9

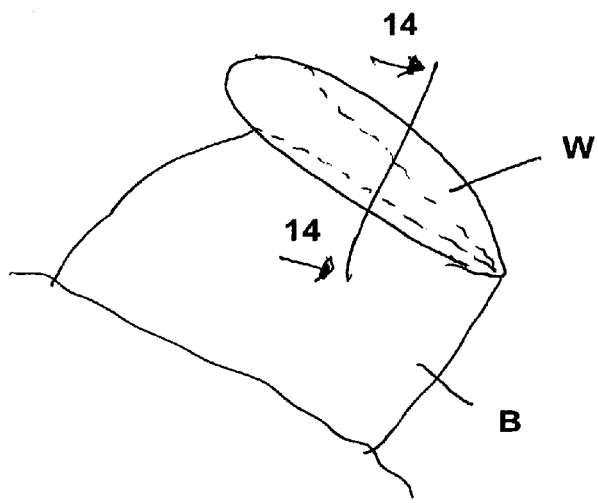
Fig. 13
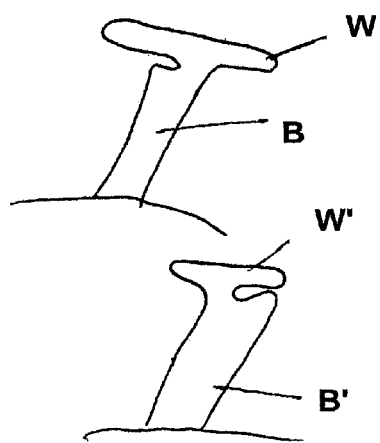
Fig. 14
(see 14-14 in Fig. 13)
Fig. 15
(see 14-14 in Fig. 13)

FLUID PUMP WITH A ROTOR

RELATED APPLICATIONS

This application is a continuation of and, pursuant to 35 U.S.C. §120, claims the benefit U.S. patent application Ser. No. 14/275,182, filed on May 12, 2014. Application Ser. No. 14/275,182 is hereby incorporated by reference in its entirety. Application Ser. No. 14/275,182 is a continuation of U.S. patent application Ser. No. 13/132,385, filed on Jul. 26, 2011, now U.S. Pat. No. 8,721,516 issued May 13, 2014. Application Ser. No. 13/132,385 and U.S. Pat. No. 8,721,516 are hereby incorporated by reference in their entireties. Application Ser. No. 13/132,385 is a 371 national phase entry of International Application PCT/EP09/008858, filed on Dec. 4, 2009. International Application PCT/EP09/008858 is hereby incorporated in its entirety. International Application PCT/EP09/008858 claims priority to U.S. Provisional Appln. No. 61/120,095, filed on Dec. 5, 2008 and EP application 08075923.6, filed on Dec. 5, 2008. Both U.S. Provisional Appln. No. 61/120,095 and EP application 08075923.6 are hereby incorporated by reference in their entireties.

FIELD OF THE INVENTION

The invention resides in the field of fluid pumps and relates to a pump which is variable with respect to the rotor diameter thereof in order to be able to be guided for example through narrow openings, such as tubes, in particular blood vessels, and to be able to be operated in the expanded state after being guided through.

The invention can hence be provided, on the one hand, in the medical field, for example as blood pump for heart support, in a minimally invasive manner, however, on the other hand, use in agitators or as a propulsion element for ships is also conceivable.

The invention can exhibit particular advantages in the medical field as a result of possible miniaturisation.

BACKGROUND OF THE INVENTION

After introducing the fluid pump through a large blood vessel into the ventricle and subsequently setting it in operation after expansion of the rotor, the pumping power of a heart can be assisted there considerably for example in humans or can be partially replaced. The therapeutic advantage of such applications resides in an at least partial relief of the heart muscle.

Expandable fluid pumps of this type are known from the state of the art already. For example, a pump emerges from DE 10 059 714 C1 which can be pushed through a blood vessel together with the pump drive. The blood flows there through a cannula, the diameter of which can be expanded and compressed in order to change the flow ratios.

A blood pump, the rotor of which can be compressed and expanded radially, is known from WO 03/103745 A2, different constructions being proposed there in order to achieve the expandability. For example by means of different mutually displaceable parts of the catheter after introduction, compressing of the pump housing and radial widening, associated therewith, can be effected. On the other hand, by rotating a drive shaft relative to a wire located in the catheter, the possibility is disclosed of producing a helix structure of the wire, the wire carrying in addition a membrane which forms a rotor blade after assuming the helix structure.

In addition, a rotor structure having a plurality of blades which are rigid per se and articulated pivotably on a central part is known from the document, said blades being deployed during operation and hence producing a fluid pressure.

A pump is known from EP 0 768 900 B1, in which rotor blades are articulated on a shaft within a pump housing in such a manner that they can be folded against the shaft in the inoperative state and, during operation, can be deployed perpendicular to the shaft in order to convey the fluid.

From US 2006/0062672 A1, a rotor of a fluid pump is known with blades that are pliably fixed to a hub and that are deployed by the fluid counterpressure generated by initial rotation of the rotor.

It is common to the known state of the art that rotor blades of a pump are pivoted either by means of a pivot mechanism for expansion or by fluid counterpressure during rotation or are formed by a mechanical device in the manner of a Bowden cable or the like only for expansion of the pump.

The object underlying the present invention with the background of the state of the art is to produce a fluid pump having a rotor which can be compressed with respect to the diameter thereof, which is built as simply as possible constructionally, which preferably comprises biocompatible materials like the pump housing surrounding it, the expansion and compression of which housing can be effected as simply as possible and which has the necessary reliability during operation.

SUMMARY OF THE INVENTION

The object is achieved according to the invention by the features of patent claim 1.

In addition, the invention relates to methods for operating the fluid pump according to the invention according to claim 16, 17 or 18.

The knowledge underlying the invention is that as simple a structure as possible of the fluid pump can be achieved by deformability of a rotor blade itself. The rotor of the fluid pump has, for this purpose, at least one rotor blade which is located in a first state as long as the rotor assumes a first, compressed state, the rotor blade assuming a second state during transition of the rotor into an expanded state by means of deformation.

The rotor blade is thereby transferred from the first state into the second state by the fluid counterpressure which occurs during rotation of the rotor during the pump operation.

A particular advantage of the invention resides in the fact that no actuation elements require to be provided for expansion of the rotor apart from the actual drive of the pump and in the fact that, due to the deformability of the rotor blade or blades per se, also no pivotable articulation of rotor blades to other parts of the pump requires to be provided.

The deformation of the blade is facilitated and at the same time delimited by providing a leading and a trailing side of the blade in the direction of movement during the conveying operation, wherein said sides have different configurations in the form of different material properties and/or constructional assembly at least along a part of the distance between the radially outer tip of the blade and the radially inner end of the blade.

The delimitation should thereby advantageously be, due to deformation, where a shape of the rotor which permits optimum conveying power is adopted. In other words, the deformability of the at least one rotor blade is advantageously delimited in such a manner that the deformation does not go beyond the shape in which the rotor produces the greatest possible fluid counterpressure.

When the fluid pump is being guided through a tube, for example a blood vessel, also no attempt is made by the rotor to expand without external influences. Such an attempt would not be desirable in medical use since the walls of the blood vessels through which the pump is guided should not be damaged. When applying through a tubular artificial access (valve), the described restoring forces would represent a particular difficulty since, as a result, high frictional forces would be produced on the wall of the artificial tubes and significant forces would require to be produced to feed the fluid pump into the interior of the body.

As long as the pump is not being operated, i.e. is not rotated on the pump shaft, the rotor remains in the compressed state and can be fed through the blood vessel.

If the pump is put in operation in situ, then the rotor is actuated in the conveying direction and the rotor blade or blades are deformed by the fluid counterpressure and hence deployed, as a result of which the actual, extensive conveyance is set in motion. It is thereby advantageous if the deformation of the rotor blade/blades is elastic since, in many application cases, the fluid pump must be compressed again after application in order to be removed.

In this case, the rotor blade/blades assumes/assume their first state again, in which the rotor is compressed, after ceasing the pump operation and stopping the rotor.

Normally, the side of the rotor blade which is leading during operation (high pressure side) is predominantly subjected to tension whilst the trailing side (suction side) is subjected to a compressive stress. The interface between the leading and the trailing sides can thereby be imagined as where a neutral load is present in the pump operation. This interface must absorb corresponding transverse and shear stresses.

It can be provided for example that the leading side and the trailing side of the rotor blade are glued to each other in the region of the interface or are connected to each other by other joining techniques.

The properties of the rotor blade which are advantageous for the invention can be achieved for example in that the leading side of the at least one rotor blade comprises a first material and the trailing side comprises a second material which is different from the first. The two materials may be both different plastic, for example polymers with different properties, for example with different additives or one of them reinforced by fibers. It is also possible that one of the layers—preferably on the trailing side—comprises an elastomer and the other layer a polymer. The rotor blade also could be made of several thin layers of plastic material wherein each layer has different properties, e.g. a first layer with a low parameter, a second layer with a parameter higher than the first, a third layer with a parameter higher than the second layer etc. (the parameter may be any mechanical property or the like). If these layers are thin enough, the change of parameter over the thickness of the blade is (at least on a macroscopic scale) continuous. Such a plurality of layers may be manufactured by spraying and/or sputtering etc. of different materials for each layer.

It proves to be advantageous if the first material is more ductile than the second material.

The first material should thereby have a permanent elongation limit so that, during deformation of the rotor blade, a limit which is as precisely defined as possible is achieved during the pump operation and a defined shape of the rotor blade is set during operation. Such a permanent elongation limit is provided for example by a non-linear range of the coefficients of elasticity of the material so that the force required for elongation increases superproportionally from a specific permanent elongation limit and the shape is stabilised as a result. This property can be intrinsic to the first material but it can be assisted or essentially produced in that stretch-resistant fibres are embedded in the first material, said fibres being substantially more stretch-resistant than the first material itself and being present unstretched in the first state of the rotor blade and in stretched form in the second state in the first material. Such fibres can be formed for example by high-strength plastic materials or by glass or by carbon fibres.

The second material on the trailing side of the rotor blades can be incompressible or be deformable only up to a specific compressibility limit. The deformability is advantageously elastic. The compression limit can be formed for example by a non-linearity of the compression coefficients in that the force required for the compression rises superproportionally from a specific compression degree.

It may also be advantageous if a first layer of material on the leading side and a second layer of material on the trailing side are provided wherein the second layer comprises trenches that allow for compression of said second layer up to the extent that the trenches are closed.

The trenches may be tangential to a circumferential direction of the rotor in order to allow for a bending of the rotor blade(s) along their radial length.

It can also be provided advantageously that the at least one rotor blade has, on the trailing side, shaped elements which are at a spacing from each other in the first state and abut against each other in the second state.

These shaped elements can be separated from each other in the first state by slots or also be embedded in a compressible material. At any rate they delimit further deformability of the rotor blade in that they abut against each other in the second state.

A further advantageous embodiment of the invention provides that at least one stop element is mounted on one side of the at least one rotor blade, said stop element penetrating the interface between the leading side and the trailing side and being moveable in a limited manner in a recess on the other side of the rotor blade.

The stop element is advantageously produced from a material which is virtually as incompressible or precisely as incompressible as the material which the trailing side of the rotor blade comprises in order to achieve a defined stop position. The stop element can comprise for example a metal or a hard plastic material.

The invention relates, apart from to a fluid pump, in addition to a method for operating a fluid pump of the described form, the pump being started by rotation of the rotor in the operating direction and the rotor being expanded by the fluid counterpressure.

It can also be provided in addition that, in order to reduce the rotor diameter, the rotor is actuated in the direction opposite to the operating direction.

It is hence made possible by the invention that, when the pump is guided through an opening, in particular a blood vessel, the rotor is actuated in the direction opposite to the operating direction and hence is compressed.

The invention may also comprise that at least one rotor blade comprises at least one winglet for optimizing the fluidic conditions (see FIGS. 13/14 in which "W" denotes a winglet and "B" denotes a blade). FIG. 15 shows an alternative embodiment with a winglet W' which is only on the leading side of the blade B'.

It may be advantageous that the at least one winglet protrudes from the leading side and/or from the trailing side of the blade.

The fluidic conditions between the rotor and the inner wall of a pump housing are best optimized by that at least one winglet is positioned at the tip of the blade. This winglet may also provide a bearing for the rotor insofar as it is gliding at the inner wall of the pump housing. However, winglets may also be provided between the tip and the radially inner end of a blade where they can influence the fluid flow.

The winglets may be fixed pivotable with regard to the blade and maybe easily pivoted into their operating position by fluid pressure that is generated when the rotor is rotating (see FIGS. 14 and 15).

The current invention also refers to a method for making a fluid pump as it has been described above.

BRIEF DESCRIPTION OF THE DRAWINGS

The invention is illustrated subsequently in a drawing with reference to an embodiment and is explained subsequently.

There are thereby shown.

DETAILED DESCRIPTION

Figure 1:
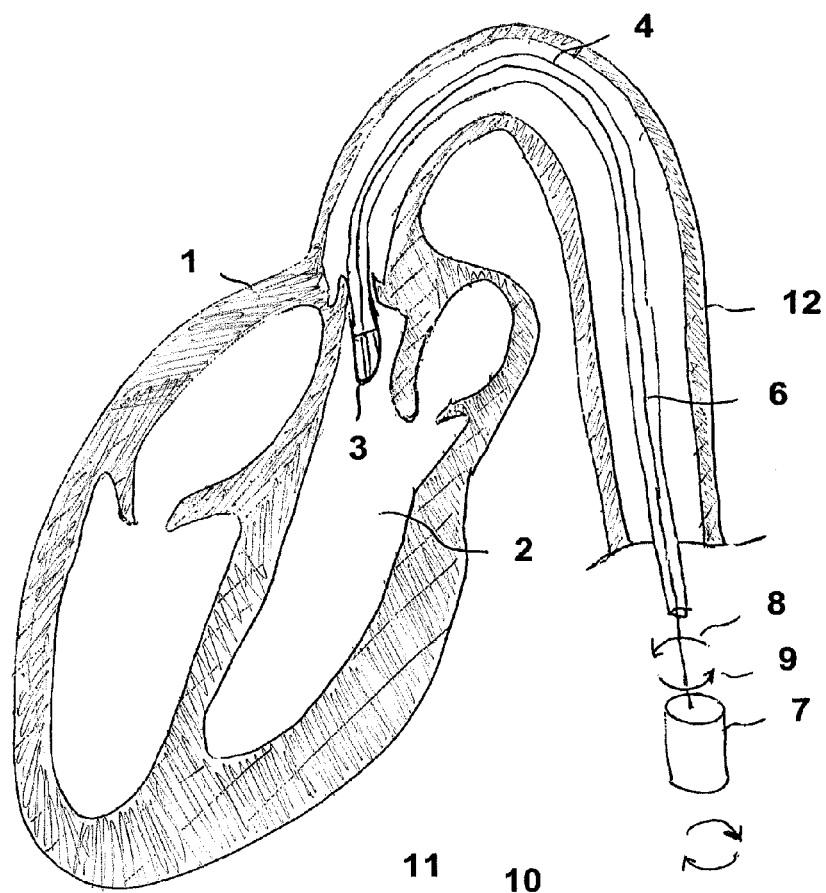
FIG. 1 schematically, the application of a fluid pump in a heart for conveying blood, FIG. 2 schematically, a pump head in longitudinal section with radial inflow, FIG. 2a schematically, a pump head in longitudinal section with axial inflow, FIG. 3 schematically, a rotor with two rotor blades in a plan view, FIG. 4 a rotor in a lateral view, FIG. 5 a section through a part of a rotor blade, FIG. 6 a section through a part of a rotor blade in a different embodiment, FIG. 7 a section through a part of a rotor blade, FIG. 8 a sectional enlargement of the detail described in FIG. 7 with VIII, FIG. 9 a section through a rotor blade in a further embodiment, FIG. 10 an embodiment of a rotor with a helical rotor blade which is supported by shaped elements, FIG. 11 a rotor, the helical blade of which is supported by a spiral winding, FIG. 12 a rotor, the helical rotor blade of which is supported by a connecting member guide, FIG. 13 a perspective view of a blade with a winglet, FIG. 14 a sectional view of the device of FIG. 13, FIG. 15 a sectional view of an alternative design of a blade/winglet.

FIG. 1 shows schematically in cross-section a heart 1, in which the head 3 of a fluid pump protrudes into a ventricle 2. The pump head 3 is disposed at the end of a cannula 4 and has a pump housing 5 which is rounded at the front.

The drive of the pump is effected via a drive shaft 6 which extends longitudinally through the cannula 4 and is connected externally to a motor 7.

The motor 7 can be actuated in both directions 8, 9, conveyance of fluid actually taking place merely in one direction of rotation.

Figure 2:
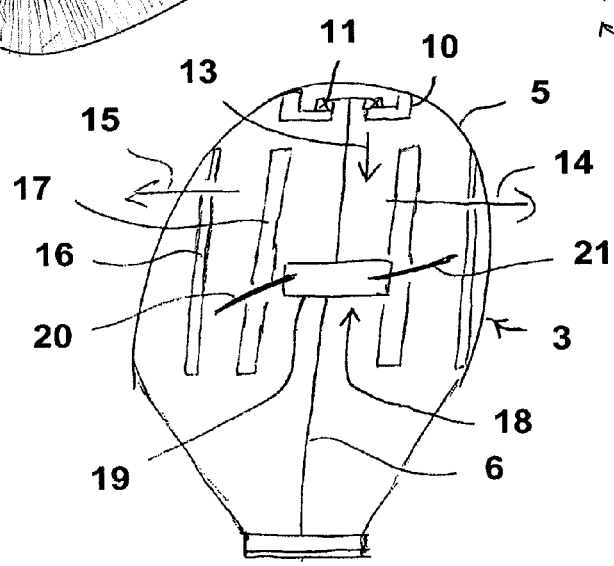

The pump head 3 with the pump housing 5 is shown schematically in FIG. 2 in longitudinal section and also the drive shaft 6. The latter is mounted rotatably at the front end of the pump head 3 in a bearing block 10 by means of a bearing 11.

FIG. 2 shows the pump head in an expanded form, i.e. with enlarged radius relative to the representation of FIG. 1.

For introduction of the pump head 3 through a blood vessel 12 into the heart, the pump head 3 is compressed radially by making the shaft slack or by axial pressure on the shaft, i.e. is brought into the state of its lowest possible radial elongation.

If the pump head has arrived at the desired location, then the pump housing can be drawn together axially by applying a tension in the direction of the arrow 13 and consequently can be expanded radially, as indicated by the arrows 14, 15.

Figure 2A:
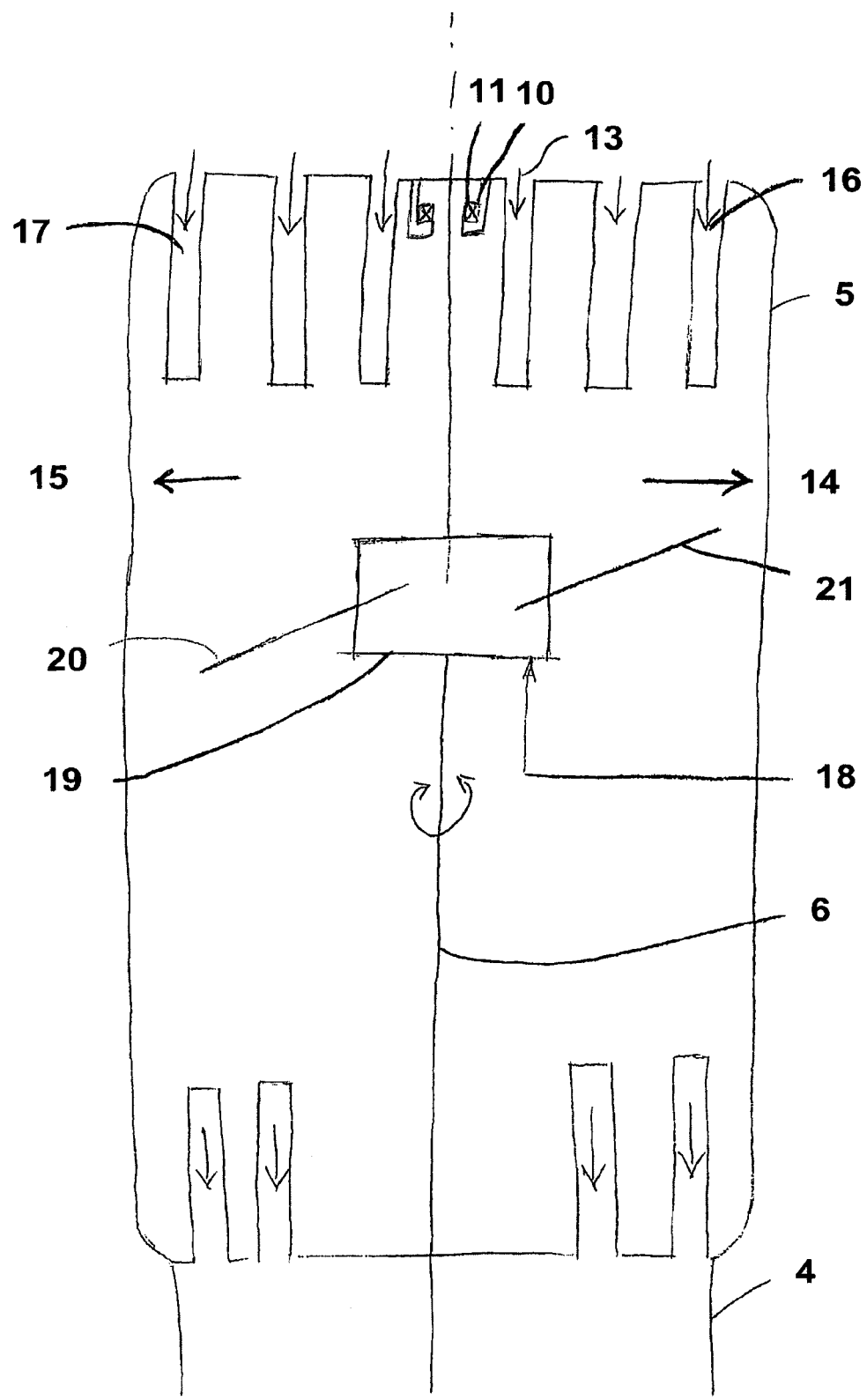

Compression and expansion of the housing by deformation of the housing is also conceivable, by means of using shape memory materials. The resilient behaviour of shape memory materials at specific temperatures is hereby exploited. Through the slots 16, 17 which extend in the axial direction of the shaft 6, fluid, i.e. in the present case blood, can pass through the pump housing 5 towards the rotor 18 of the pump and can be conveyed further through the latter, for example axially through the cannula 4. In FIG. 2, the inflow of the rotor has a radial configuration. In FIG. 2a, an embodiment with axial inflow and outflow is represented schematically.

The rotor has a rotor blade carrier 19 and also rotor blades 20, 21, the rotor blades 20, 21 being folded out during pump operation, i.e. in the expanded state of the rotor.

The radius of the rotor during operation is coordinated to the internal diameter of the pump housing in the expanded state thereof.

If the pump head is intended to be removed from the heart 1, then the pump operation is ceased and the rotor blades 20, 21 abut against the rotor blade carrier 19 in order to reduce the radius of the rotor 18. This is advantageously assisted by rotation of the rotor 18 in the direction of rotation opposite to the pump operation.

If the shaft 16 is then displaced towards the pump head 3 in the manner of a Bowden cable, then the pump head again assumes its compressed form and can be removed through the blood vessel 12.

Figure 3:
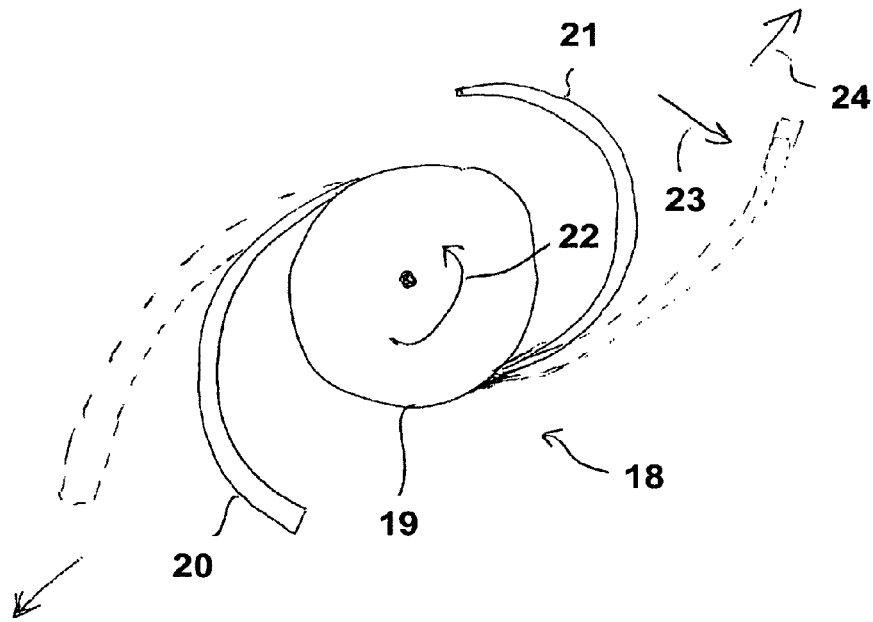

FIG. 3 shows in detail a plan view on the rotor 18 with the rotor blade carrier 19 and the rotor blades 20, 21, these being represented in a continuous shape in their first state, i.e. the compressed state of the rotor. The rotor blades can also abut even more closely against the rotor blade carrier 19 in the first state.

It is important that, when the pump operation and rotation of the rotor 18 starts, in the direction of rotation 22 required for the conveyance operation, a fluid counterpressure is produced in the direction of the arrow 23 towards the rotor blades and these are bent by widening the radius of the rotor 18. If the pump is designed as a radial pump, then the fluid is displaced and hence conveyed radially outwards in the direction of the arrow 24.

Figure 4:
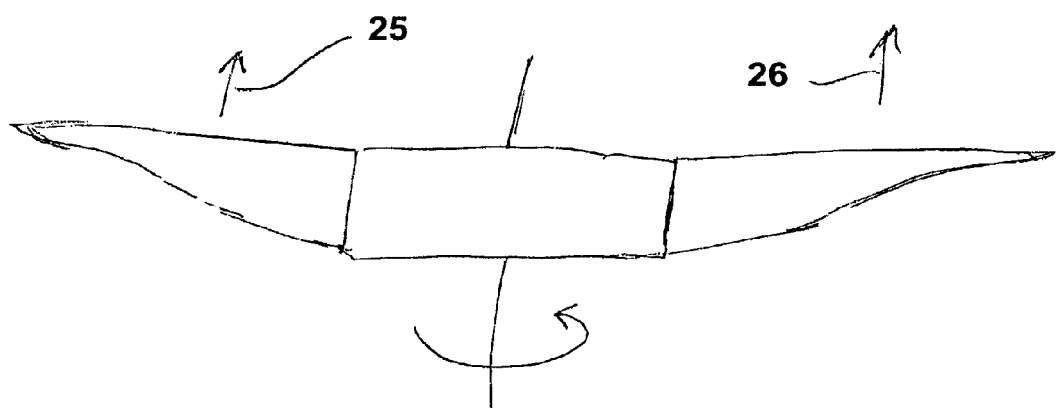

If the rotor blades 20, 21 are profiled in the axial direction, then the fluid can be conveyed also in the axial direction, as indicated in FIG. 4 by the arrows 25, 26.

If the rotor is operated in a direction of rotation opposite to the direction of rotation 22 required for the conveyance, then a fluid counterpressure is produced on the rotor blades 20, 21, said counterpressure being opposite to the direction 23 and leading to the rotor blades folding up against the rotor blade carrier 19 and to a corresponding reduction in the rotor diameter. In this state, the rotor can be removed with a correspondingly compressed pump housing 5 out of the heart through the bloodstream.

By choice of the direction of rotation and the speed of rotation, the diameter of the rotor can hence be specifically changed, on the one hand, and, on the other hand, the conveyance power of the pump can be adjusted as desired.

FIG. 5 shows, by way of example, a rotor blade 21 with one side 27 which is leading during the pump operation and also a trailing side 28, the rotor blade having, along an interface 29, different properties on both sides thereof. During operation, a fluid counterpressure acts on the rotor blade in the direction of the arrow 23 and deforms the latter in the second state in which the rotor is expanded. For this purpose, the leading side 27 must be able to be elongated to a specific degree and the corresponding first material layer 30 has membrane properties for this reason. This first material layer can involve for example rubber or an elastic plastic material which is elastically deformable up to a permanent elongation limit and resists further elongation thereafter as far as possible.

On the trailing side 21, the second material layer 31 comprises a compression-resistant material which is configured for example to be so hard that it is deformed only minimally when forces are acting during operation so that bending of the rotor blade is produced exclusively via the elongation of the first material layer 30.

However, a certain compressibility of the second material layer 31 can be provided.

FIG. 6 shows a further example for configuration of a rotor blade in which notches 32 are provided in the second material layer 31, which allow compression and bending of the trailing side until the notches 32 are closed and the various webs formed between the notches 32 abut against each other in a form fit. In this state, further bending of the rotor blade would be stopped.

The material of the first material layer 31 in this case can likewise be a hard plastic material from which parts are cut out or recessed in a casting or embossing process.

In this case also, the material of the first material layer 30 comprises a material which can be elongated to a limited extent.

In FIG. 7, a rotor blade is represented in cross-section, the detail VIII in FIG. 8 being shown in more detail. The detail VIII thereby shows the compression-resistant second material layer 31a which, for its part, has a multilayer construction in the manner of a sandwich structure, the latter comprising tension- and/or compression-resistant external layers 33, 34, 35, 36 and also a volume layer 37. The external layers 35, 36 can be reinforced for example with a woven material.

A very compression-resistant layer is hence formed on the trailing side so that the deformability of the rotor blade is determined essentially by the ability of the leading side 27 to elongate.

In FIG. 9, a variant is represented in which a stop element 38 is mounted in the first layer 30, for example by means of a countersunk screw 39, the stop element 38 protruding into an opening 40 of the second layer 31.

If the rotor blade 21 is deformed, then the opening 40 in the second material layer 31 will tend to be reduced and displaced until the edges of the opening 40 abut against the stop element 38. The stop element comprises a hard material just like the second material layer 31 so that, after abutment, no further compression is possible on the trailing side and the paddle blade is reinforced against further deformation.

Figure 10:
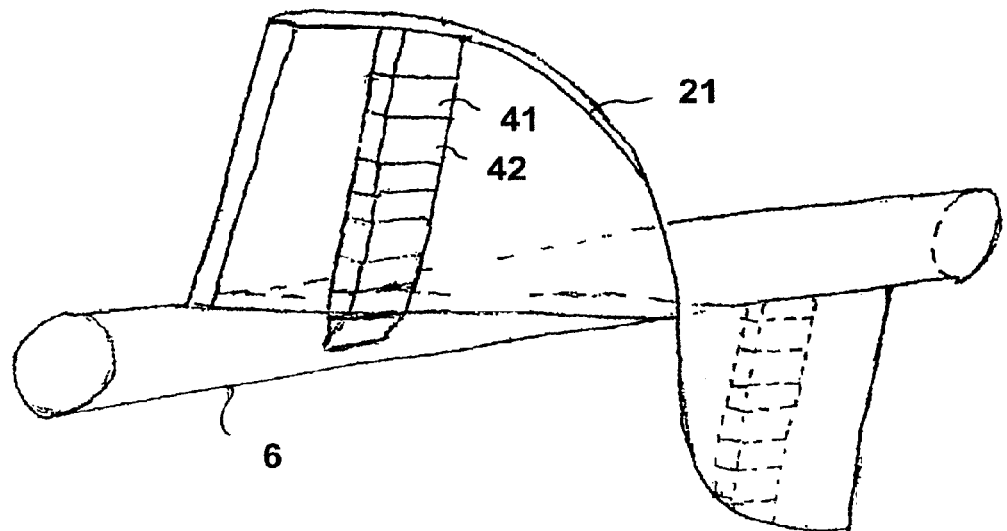

FIG. 10 shows a helical rotor blade in which a series of shaped elements 41, 42 on the trailing side of the blade are connected to each other, for example glued, or applied with a different joining method. In the compressed state of the rotor, a spacing exists between the shaped elements respectively. During operation of the pump and after deploying the blade, the shaped elements abut against each other and are reinforced as a continuous web which supports the flat parts of the blade acting as membrane and prevents further deformation. A plurality of such rows of shaped elements can be disposed along the drive shaft 6 axially and offset azimuthally.

Figure 11:
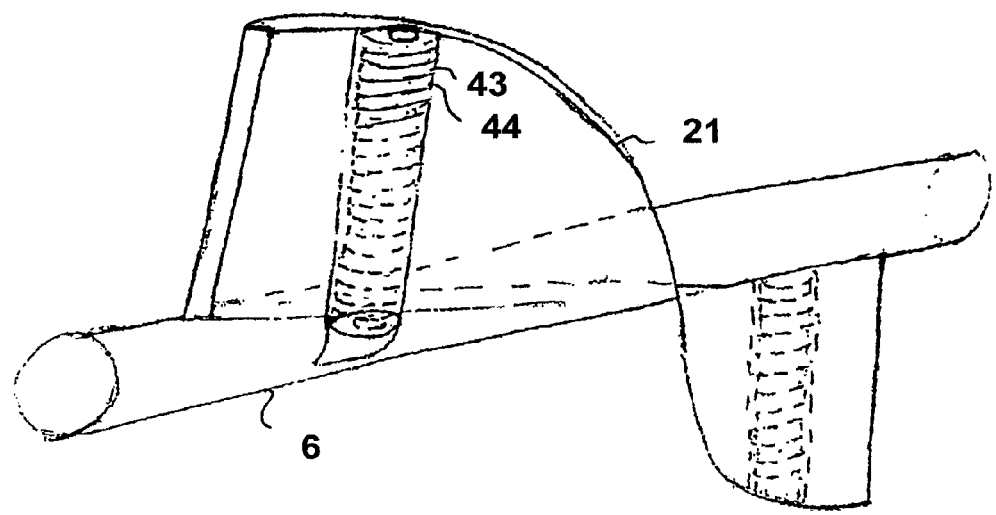

A similar construction is shown in FIG. 11 where the web, for strengthening the rotor blade, is formed by a winding 43 comprising coils 44, for example comprising a plastic material, a spring wire or a hose. The individual coils 44 respectively form one shaped element and are connected individually to the membrane-like surface of the rotor blade by gluing.

During compression of the rotor, the gussets between the windings 43 open, and these close during deployment of the blade. In order to stabilize the winding 43, a continuous core is provided within the latter, said core being able to be flexible.

Figure 12:
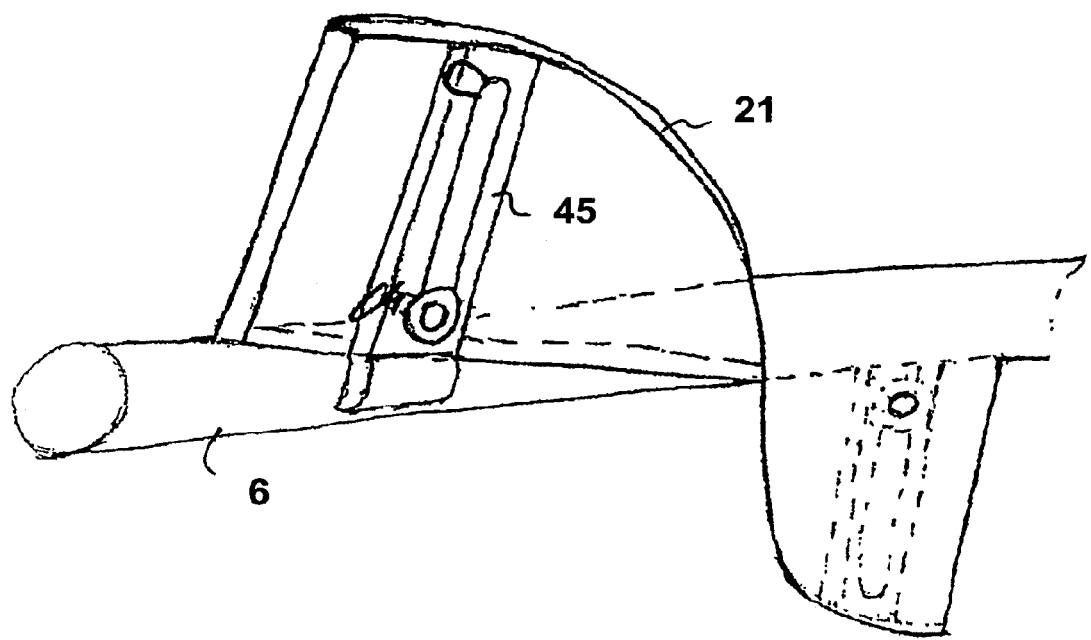

FIG. 12 shows the support of the rotor blade by a solid rail/connecting member 45 in which a stop element is moveable in a limited fashion. The stop element is connected to the rotor blade.

The rail/connecting member 45 can be configured, relative to the forces and moments which act as expected, as bend-resistant and compression-resistant component. As a result of the bending, small additional restoring forces are produced in this embodiment. Because of the low material thickness, regarded in absolute terms, few restoring forces are produced.

In FIG. 12, the stop element is located in the lower position. Bending up to the bent situation would require high acting forces for this position due to the small length between connecting member take-up on the shaft 6 and position of the guide pin in the rail/connecting member 45.

The mentioned and described constructions of rotor blades are examples of how, by means of different configuration of the various sides of the rotor blades, a limited deformability during operation can be achieved by the fluid counterpressure.

During rotation of the rotor in a direction opposite to the operating direction, the deformation of the rotor blades is reversed and these abut against the rotor, assume a first state and hence define the compressed state of the rotor in which the latter can move easily through a narrow opening, for example a blood vessel or a tubular artificial access (valve).

Hence the invention allows, in a constructionally particularly simple manner, production of a rotor which can be varied in its diameter for various applications, but particularly advantageously for the medical field.

What is claimed is:

1. A fluid pump, comprising a rotor with at least one rotor blade for conveying fluid, the rotor being variable with respect to its diameter between a compressed state, and an expanded state, wherein the at least one rotor blade deforms as the rotor transitions between the compressed state, and the expanded state, wherein the at least one rotor blade has a leading side and a trailing side with respect to the direction of rotation during conveying pump operation, and wherein the rotor is configured such that when the rotor is rotating during conveying pump operation, the fluid counterpressure is produced counter to the direction of rotation against the leading side of the at least one rotor blade, and wherein the rotor comprises a first material, wherein the first material comprises fibers.

2. The fluid pump of claim 1 wherein the fibers are stretch-resistant.

3. The fluid pump of claim 2 wherein the stretch-resistant fibers are more stretch-resistant than the first material.

4. The fluid pump of claim 2 wherein the stretch-resistant fibers are selected from the group comprising: high-strength plastic fibers, glass fibers, and carbon fibers.

5. The fluid pump of claim 2 wherein the stretch-resistant fibers are unstretched in the compressed state of the rotor.

6. The fluid pump of claim 2 wherein the stretch-resistant fibers are stretched in the expanded state of the rotor.

7. The fluid pump of claim 1 wherein the leading side is comprised of the first material and the trailing side is comprised of a second material.

8. The fluid pump of claim 7 wherein the first material differs from the second material.

9. The fluid pump of claim 1 wherein the rotor is variable with respect to its diameter between a compressed state, a first expanded state, and a second expanded state.

10. The fluid pump of claim 9, wherein the second expanded state is achieved by means of a fluid counterpressure resulting from conveyance of fluid during rotation of the rotor during conveying pump operation.

11. A fluid pump, comprising a rotor with at least one rotor blade for conveying fluid, the rotor being variable with respect to its diameter between a compressed state, and an expanded state wherein the at least one rotor blade has a leading side and a trailing side, and wherein the leading side is made from a first material and wherein the first material comprises fibers.

12. The fluid pump of claim 11 wherein the fibers are stretch-resistant.

13. The fluid pump of claim 12 wherein the stretch-resistant fibers are more stretch-resistant than the first material.

14. The fluid pump of claim 12 wherein the stretch-resistant fibers are selected from the group comprising: high-strength plastic fibers, glass fibers, and carbon fibers.

15. The fluid pump of claim 12 wherein the stretch-resistant fibers are unstretched in the compressed state of the rotor.

16. The fluid pump of claim 12 wherein the stretch-resistant fibers are stretched in the expanded state of the rotor.

17. The fluid pump of claim 11 wherein the leading side is comprised of the first material and the trailing side is comprised of a second material.

18. The fluid pump of claim 17 wherein the first material differs from the second material.

19. The fluid pump of claim 11 wherein the rotor is variable with respect to its diameter between a compressed state, a first expanded state, and a second expanded state.

20. The fluid pump of claim 19, wherein the second expanded state is achieved by means of a fluid counterpressure resulting from conveyance of fluid during rotation of the rotor during conveying pump operation.

21. The fluid pump of claim 20 wherein the stretch-resistant fibers are stretched in the second expanded state of the rotor.

22. A fluid pump, comprising a rotor with at least one rotor blade for conveying fluid, the rotor being variable with respect to its diameter between a compressed state, a first expanded state, and a second expanded state, wherein the at least one rotor blade deforms as the rotor transitions between the compressed state, the first expanded state, and the second expanded state, and wherein the second expanded state is achieved by means of a fluid counterpressure resulting from conveyance of fluid during rotation of the rotor during conveying pump operation, wherein the at least one rotor blade has a leading side and a trailing side with respect to the direction of rotation during conveying pump operation, and wherein the rotor is configured such that when the rotor is rotating during conveying pump operation, the fluid counterpressure is produced counter to the direction of rotation against the leading side of the at least one rotor blade and the at least one rotor blade is resultingly deformed so as to widen the diameter of the rotor, and wherein the leading side comprises a first material and the trailing side comprises a second material and wherein the first material differs from the second material.

23. The fluid pump of claim 22, wherein the first material comprises fibers.

24. The fluid pump of claim 23 wherein the fibers are stretch-resistant.

25. The fluid pump of claim 24 wherein the stretch-resistant fibers are more stretch-resistant than the first material.

26. The fluid pump of claim 24 wherein the stretch-resistant fibers are selected from the group comprising: high-strength plastic fibers, glass fibers, and carbon fibers.

27. The fluid pump of claim 24 wherein the stretch-resistant fibers are unstretched in the compressed state of the rotor.

28. The fluid pump of claim 24 wherein the stretch-resistant fibers are stretched in the second expanded state of the rotor.

* * * * *